(12) United States Patent
Hewitt

(10) Patent No.: US 6,756,194 B2
(45) Date of Patent: Jun. 29, 2004

(54) CONTROL SAMPLES FOR USE AS STANDARDS FOR EVALUATING APOPTOSIS IN A SELECTED TISSUE

(75) Inventor: Charles W. Hewitt, Blackwood, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/903,381

(22) Filed: Jul. 11, 2001

(65) Prior Publication Data

US 2003/0017462 A1 Jan. 23, 2003

(51) Int. Cl.$^7$ .............................. A01N 1/00; G01N 1/30
(52) U.S. Cl. ..................... 435/1.1; 435/40.52; 435/40.5
(58) Field of Search .............................. 435/1.1, 40.52, 435/40.5

(56) References Cited

U.S. PATENT DOCUMENTS

| | | | |
|---|---|---|---|
| 5,437,998 A | 8/1995 | Schwarz et al. | 435/286 |
| 5,763,279 A | 6/1998 | Schwarz et al. | 435/383 |

OTHER PUBLICATIONS

Lee, "Tissue–engineered human living skin substitutes: development and clinical application", Yonsei Medical Journal 41 (6): 774–779 (2000).*

Doolin et al., "The Effect of Leukocyte Infiltration on Apoptosis in an In Vitro Thermal Injury Bioartificial Living Skin Equivalent Model," Journal of Burn Care & Rehabilitation, vol. 20, No. 6, (Sep.–Oct. 1999) pp. 364–376.

Doolin et al., "Effects of Microgravity on Growing Cultured Skin Constructs," Tissue Engineering, vol. 5, No. 6, (1999) pp. 573–581.

Doolin et al., "Morphometry and Histochemistry of Pulmonary Arteries in a Hypoplastic Lung Model," Journal of Surgical Research, vol. 59, No. 1, (Jul. 1995) pp. 191–197.

Krajewski et al., "Prognostic significance of apoptosis regulators in breast cancer," Endocrine–Related Cancer, vol. 6, (1999) pp. 29–40.

Strande et al., "In Vitro Bioartificial Skin Culture Model of Tissue Rejectiona dn Inflammatory/Immune Mechanisms," Transplantation Proceedings, vol. 29, (1997) pp. 2118–2119.

* cited by examiner

Primary Examiner—Sandra E. Saucier
(74) Attorney, Agent, or Firm—Michael J. Wise; Perkins Coie LLP

(57) ABSTRACT

A method for producing standard control samples to be used to evaluate disease states or trauma that involve apoptosis or suppression of apoptosis is disclosed. Also disclosed are standard control samples produced by the method. The control samples comprise natural or artificial tissues treated in vitro to display reproducible, predetermined indicators of apoptosis that are equivalent to indicators of apoptotic status of corresponding tissues and organs of a living subject.

2 Claims, No Drawings

CONTROL SAMPLES FOR USE AS STANDARDS FOR EVALUATING APOPTOSIS IN A SELECTED TISSUE

FIELD OF THE INVENTION

The present invention relates generally to the fields of medicine and pharmacological research. More specifically, the invention provides standard control samples to be used to evaluate disease states or trauma that involve apoptosis or suppression of apoptosis. The control samples comprise natural or artificial tissues treated in vitro to display reproducible, predetermined indicators of apoptosis that are equivalent to indicators of apoptotic status of corresponding tissues and organs of a living subject.

BACKGROUND OF THE INVENTION

Several scientific or patent publications are referenced in this patent application to describe the state of the art to which the invention pertains. Each of these publications is incorporated by reference herein, in its entirety.

A coordination and balance between cell proliferation and cell death is critical for normal development and homeostasis of tissues and organs. Abnormalities in either of these processes may cause tissue atrophy or hypertrophy, either of which can lead to cancer, autoimmune disease or degenerative disorders.

It is becoming increasingly apparent that the processes of cellular proliferation and programmed cell death, i.e., apoptosis, are linked by many common signaling mechanisms. Thus, up-regulation of one process may be accompanied by down-regulation of the other, leading to the ultimate expression of a disease state or pathological condition. For instance, increased cell cycling due to overexpression of the c-myc oncogene and reduced apoptosis due to bcl-2 oncogene deregulation are two factors observed in the development of lymphomas and mammary tumorigenesis.

A variety of disease states and other pathological conditions are linked to dysregulated apoptosis in a particular tissue or organ. These include, for example, general conditions related to tissue rejection, immune/inflammatory responses, ischemia and injury, cardiovascular diseases such as dilated or ischemic cardiomyopathy, myocarditis and atherosclerosis, neurodegenerative disorders such as ALS, Alzheimer's disease, Parkinson's disease and retinal degeneration, hepatic and pancreatic disorders related to viral infection or alcohol consumption, which can lead to development of insulin-dependent diabetes mellitus or infection with certain viruses, such as adenoviruses, influenzaviruses and human immunodeficiency virus.

Additionally, a variety of cell proliferative diseases and disorders are linked to dysregulated apoptosis. These include, for example, psoriasis, lupus and other autoimmune conditions such as Crohn's disease, Hashimoto's thyroiditis and arthritis, infection with certain viruses, such as human papillomavirus, Epstein-Barr virus and herpes simplex virus; as well as a variety of cancers, including mammary carcinomas, lymphomas cervical and ovarian cancers, and neuroblastomas. As mentioned above, such proliferative deseases may be marked by a decrease in apoptosis in the affected tissue or organ, and may also be identified by up-regulation of enzymes and signaling molecules involved in cell growth or cell cycling.

Clearly, the apoptotic status of a particular tissue is relevant to the diagnosis and prognosis of type and severity of a wide variety of diseases or physiological conditions. Moreover, the efficacy of a selected therapeutic regime for treating such disease may be evaluated by assessing the apoptotic status of the tissue. For this reason, morphological and biochemical markers of apoptosis and mitosis are of great interest to investigators in their attempts to devise clinically relevant diagnostic and prognostic indicators of disease status in a patient.

In the development of clinically relevant models of disease states, current technology utilizes cultured cell lines, or tissues from subjects having a particular disease, or animal models to evaluate a particular pathological condition and/or to develop agents to treat the condition. Each of these methodologies has certain limitations.

For instance, cultured cell lines are often utilized for screening therapeutic agents and for studying the cellular physiology associated with diseases involving tissues comprising the cell type. The information gathered from the use of cultured cell lines is of limited value, however, because the physiological profile of cells in culture often does not accurately reflect the physiological profile of corresponding primary cells contained in a tissue or organ.

As another example, particularly utilized in the study of tumors, it is common practice to store excised tumor tissue of a particular type for use as comparison in diagnosis of other patients or evaluation of the efficacy of a patient's therapeutic regimen. One disadvantage of this practice is the lack of appropriate standardized controls. The excised tumor sample represents the end result of a disease progression. As such, it is of little value in diagnosis of early or intermediate stages of the disease. Furthermore, biopsied tissues can be extremely variable in their disease presentation and expression of biochemical markers of disease. Biopsied tissue also is often not readily available when needed, and moreover can present a health hazard in that it may contain infectious agents.

As another example, animal models are often used for studying a disease and developing new agents and methods of treatment. Whereas an animal model may offer biologically relevant information, their use has many disadvantages. From a practical standpoint, it is expensive and time-consuming to use animals in research. Moreover, results may not be reproducible from one animal study to another. Furthermore, there are numerous diseases and pathological conditions for which no relevant animal model exists. Finally, the use of animals in certain types of research (e.g., wound research) is increasingly being called into question for ethical reasons.

Thus, a need exists for a clinically relevant standardized control for use in evaluating the apoptotic status of a selected tissue or organ. It would be of great advantage to be able to reproducibly produce such standardized controls for any tissue or organ in which it is desirable to evaluate apoptosis. It would be of further advantage for such controls to be of high biological relevance, i.e., to display many, if not all, of the morphological and biochemical features of apoptosis as would be observed in a corresponding tissue in a living subject. Finally, such controls preferably should be capable of being standardized for incremental changes in apoptosis.

SUMMARY OF THE INVENTION

The present invention satisfies the need in the art for a clinically relevant standardized control for use in evaluating the apoptotic status of a selected tissue or organ. The invention provides compositions that can serve as standardized controls for any tissue or organ in which it is desirable to evaluate apoptosis. The controls are of high biological relevance, in that they display a variety of morphological and biochemical features of apoptosis, and can display incremental changes in apoptosis.

Thus, one aspect of the invention features a composition for use as a standardized measure of apoptosis in a test sample of tissue from a subject. The composition comprises at least one segment of an equivalent tissue that has been subjected to a treatment that reproducibly results in a predetermined, measurable amount of apoptosis in the segment. These tissue segments are sometimes referred to herein as "apoptosis tissue standards". In a highly preferred embodiment, they are produced by culturing the tissue segment in a microgravity bioreactor for a period of time known to produce the predetermined amount of apoptosis in the tissue segment. Other means of producing the apoptosis tissue standards are also provided in accordance with the invention, as described in detail below.

In preferred embodiments of the invention, at least two tissue segments are featured, wherein one of the segments is a negative control segment which has not been subjected to the apoptosis-inducing treatment and the other segment is a positive control segment which has been subjected to a level of the treatment that reproducibly results in a maximum amount of apoptosis obtainable in the segment as a result of the treatment. Other preferred embodiments provide intermediate control segments which have been subjected to a level of the treatment that reproducibly results in a predetermined amount of apoptosis intermediate between that of the negative control segment and that of the positive control segment.

Another aspect of the invention features a kit for evaluating apoptosis in a test sample of tissue. At minimum, the kit comprises the apoptosis tissue standard(s) described above, along with instructions for their use in evaluating apoptosis in a test sample of tissue. The kits may comprise the tissue segments themselves, or extracts of the tissues containing soluble proteins or RNA, or, optionally, culture media in which the tissue was cultured during induction of apoptosis. The kits may further comprise reagents and instructions for performing various assays relating to measuring the amount of apoptosis present in the tissues.

In other embodiments of the inventions, the kit comprises apoptosis tissue standards that have been processed for one or more assays or methods to evaluate apoptosis in a tissue. Such processing may include processing for histology, immunohistochemistry, or TUNEL staining, among others.

Other features and advantages of the present invention will be understood by reference to the detailed description of the invention and examples that follow.

DETAILED DESCRIPTION OF THE INVENTION

The present invention arises from the inventors' insightful appreciation that tissue samples induced to apoptose under reproducible conditions to display a predetermined, measurable amount of apoptosis would fill a need in the art related to the evaluation of apoptosis, or suppression thereof, in the clinical and research setting. The steps for making the apoptosis standard control tissues of the present invention are as follows:

1. Select and obtain the desired tissue;
2. Place the tissues in the desired form for subsequent treatment (e.g., prepare slices or segments of the tissue);
3. Subject the tissue to a treatment that reproducibly induces a pre-determined level of apoptosis; and
4. Collect the treated tissue samples for use; or
5. Optionally, process the samples for storage or for a specific assay or method to measure apoptosis.

As a result of the inventors' discovery that apoptosis can be induced in any tissue type by one or more of several means, apoptosis standards for any desired tissue can be produced in accordance with the present invention. These include, but are not limited to, tissues from skin, brain, heart, lung, liver, spleen, pancreas, thymus, thyroid, lymph node, stomach, kidney, bladder, intestine, colon, testis, mammary, ovary, uterus, muscle and bone, to name a few. These further include "normal" tissues; i.e., tissues that are not diseased, or abnormal tissues such as tumors. Indeed, apoptosis standard tumor tissues are expected to be of utility in clinical determinations of the efficacy of a particular anti-cancer therapy, or prognosis for a patient having such a tumor.

In a preferred embodiment, the tissue is obtained directly from a living or newly-dead organism. In another embodiment, the tissue comprises a bioartificially constructed tissue demonstrated to be equivalent to naturally occurring tissue of the same type. For instance, a bioartificial living skin equivalent (LSE), as described by Strande et al. (Transplantation Proceedings 29:2118–2119, 1997), can be utilized instead of skin taken directly from an organism.

The guideline for choosing a tissue type to use as the standardized control of the invention, whether naturally occurring or artificial, is that the tissue is equivalent to the type of tissue for which it is to serve as a standard for comparison. For instance, if the apoptotic status of liver tissue in a patient is to be evaluated, the standard control tissue also should be liver tissue. Moreover, it should be obtained from an organism of biological relevance to the patient. That is, if the patient is a human, mouse liver tissue, for example, can serve as an appropriate standard because it has been demonstrated that mammalian livers all function in essentially the same manner.

Once obtained, the tissue is prepared for treatment. Such preparation can comprise cleaning the tissue, then slicing or otherwise segmenting the tissue into appropriately sized fragments. Other similar preliminary preparations of tissues will be well understood to those of skill in the art.

Next, the tissue is subjected to the treatment that results in reproducible production of a predetermined level of apoptosis, ranging from none (negative control) to the maximum amount obtainable for the tissue type (positive control). Apoptosis can be induced in a variety of ways, many of which are controllable and reproducible. These methods generally comprise applying a biological stress to the tissue, which induces an apoptosis response.

One very useful means of applying an apoptosis-inducing biological stress is simply to culture a natural or artificial tissue in one of several culture systems. In a particularly preferred embodiment of the invention, apoptosis is induced by incubating the tissue segments in a microgravity culture system, such as that provided by the rotating cylindrical cell culture vessel (RCCS bioreactor) developed for the NASA space program, and commercially available from Synthecon, Inc. (Houston Tex.). The RCCS bioreactor is described in detail in U.S. Pat. Nos. 5,763,279 and 5,437,998 to Schwartz et al. The rotating culture vessel system creates the environment of simulated microgravity. By rotating the culture system at a constant and appropriate speed, tissue fragments are maintained in constant suspension. This achieves a state of continuous "free-fall" so that the tissue is exposed to random gravity vectors, thereby reducing the effect of gravity to approximately 0.1 G and relieving the cells or tissues from the deforming force of gravity. The rotating culture system also increases contact between the tissue and the media and reduces shear forces on the cells.

A surprising discovery made in accordance with the present invention is that, even though the RCCS bioreactor can promote growth of cultured cells and tissues, primary tissues of all types are induced to undergo apoptosis simply by incubating the tissue in the bioreactor for a period of time ranging from two to 96 hours, in most cases (though the range can be shorter or longer in some cases). Because standard incubation times that reproducibly lead to a predetermined amount of apoptosis in a given tissue can be readily determined with little effort, this method of apoptosis induction is very convenient and highly preferred for use in making the apoptotic tissue standards of the invention. The induction of apoptosis in thymic tissue utilizing incubation in the RCCS bioreactor is described in detail in Example 1. In this example, the maximum level of apoptosis, as measured by TUNEL, was achieved in 24 hours without the addition of dexamethasone, and in 10 hours in the presence of dexamethasone.

The RCCS bioreactor is suitable for use with natural or artificial tissues. Indeed, it has been shown that the bioartificial LSE (Strande et al., 1997 supra) grows as well, if not better, in the RCCS bioreactor (Doolin et al., Tissue Engineering 5: 573–581, 1999) than in static culture systems. For artificial tissues, such as the LSE, that do not naturally undergo apoptosis upon incubation in the RCCS bioreactor, apoptosis is induced by a different means (such as heat treatment as described below), and the bioreactor is used to incubate the tissues for a time sufficient to achieve the desired level of apoptosis resulting from the stress treatment.

In further embodiments, other bioreactor systems may be used, including, for example, standard impeller-type bioreactors, roller bottles, shaker baths, or hollow-fiber bioreactors. Such bioreactors are known to induce apoptosis in cell cultures; in fact, their use for mass production of cells has been limited by this problem. It should be noted that the variable induction of apoptosis that can occur in the standard bioreactor can be a disadvantage in the production of the apoptotic tissue standards of the present invention. The microgravity system allows for low shear-stress and high nutrient exchange, as tissues are cultured in small organoid fragments and consistent conditions to induce apoptosis. These parameters provide consistency and control in the microgravity system, as described above.

In yet another embodiment, a static culture system can be utilized. Static culture systems, i.e., those that do not employ agitation of the media by impeller or rotation, can biologically stress a tissue as a result of the effects of gravity or low oxygenation. If a static culture is used to induce apoptosis, this is enhanced by the application of additional stress conditions, including physical or chemical stresses such as heat, mechanical injury or other physical stresses, or induction by toxic chemicals.

Many biological stresses are also known to induce apoptosis. These include, but are not limited to, temperature stress (heat or cold), Uv irradiation, hypoxia, free-radical damage, serum deprivation and exposure to certain chemicals or biological agents, such as dexamethasone, TNFα (NB cells), hyperosmolality, Granzyme B, FAS ligand, FAS (CD95), perforin, and Trail/DR4, to name a few. Any of these biological stresses can be used, alone or in combination with each other or with a selected culture regime as described above.

In a preferred embodiment, heat is used to induce apoptosis in the tissue segments. As one example, using natural skin or the living skin equivalent (LSE) and a static culture system, apoptosis can be reproducibly induced by scalding the tissue. For instance, it has been demonstrated that scalding of natural skin or the LSE induces apoptosis, measurable as DNA damage by TUNEL assays (Doolin et al., J. Burn Care Rehabil. 20: 374–376, 1999) and by increases in apoptosis-related molecules, such as FasL and Fas (Hewitt et al., Burn Care & Rehabil. S169; Abstr. 66, 1999). In this embodiment, the tissues are subjected to the heat stress (e.g., treatment with hot PBS, up to 70° C.), then incubated in static culture or in a bioreactor for a selected period of time and under conditions known to produce a desired level of apoptosis. The amount of apoptosis in the tissue is controlled by the temperature and duration of the heat treatment and the duration of incubation in static culture or in the bioreactor.

In another preferred embodiment, a chemical treatment is used alone or in combination with another biological stress to induce apoptosis in the tissue. One example of this is set forth in Example 1, wherein 1 $\mu$M dexamethasone in the culture medium increases the rate of apoptosis of thymic tissue incubated in a RCCS bioreactor. Dexamethasone can be added to culture media in a concentration range of 0.01–100 $\mu$M, preferably 1–50 $\mu$M. Most preferably, however, the concentration is 1 $\mu$M (it is understood that 0.01–0.05 $\mu$M dexamethasone is a physiological range, 0.1–1.0 $\mu$M is a pharmacological dose range, and a high dose range is 25–100 $\mu$M).

It also is advantageous in the study and evaluation of apoptotic status in tumors to treat the control tissue samples with a mitogen or regulator of cell growth or de-differentiation, to stimulate cell proliferation. In this manner, apoptosis in a cell proliferative environment is can be mimicked, and appropriate standard control tissues generated for use in evaluating various forms of cancer. Mitogens or stimulants of cell growth or de-differentiation suitable for use in this embodiment of the invention include, but are not limited to, concanavalin A, phytohemaglutinin, endotoxins, LPS, various antibodies, various lectins, growth factors (such as PDGF, BFGF, ECGS), Il–2, $\gamma$-IFN, and many biologically or functionally similar molecules, as would be appreciated by one of skill in the art. Tissue can be pre-treated with the mitogen, or the mitogen can be introduced directly into the culture medium. The amount of such mitogenic or cell growth-promoting agents to be used depends on the specific compound, and is easily determinable by persons of skill in the art.

After the desired amount of apoptosis in a particular tissue is achieved, the tissue segments are collected and prepared for use as standard controls in the evaluation of apoptosis in test samples of tissues in the clinic or research laboratory. Such preparation may comprise simply rinsing and placing the segments in an appropriate medium, then using the segments immediately, or refrigerating them for later use. This sort of preparation enables the investigator to process the control tissue segments right along with test tissue segments for apoptosis assays in the clinical or research laboratory.

In other embodiments of the invention, the apoptotic tissue segments are prepared for one of several assays for measuring apoptosis. For instance, the tissue segments may be fixed and sectioned for histological examination, using light- or electron-microscopy. It is well known, that apoptotic cells display distinctive morphological features, which are characteristic of the stages of apoptosis ranging from early events to complete cell death.

As another example, the apoptotic tissue segments may be fixed and processed for assays that measure DNA damage, another hallmark of apoptosis. Preferred for the present invention is the processing of the tissue segments for TUNEL assays, as is well known in the art and described in Example 1.

As another example, the apoptotic tissue segments are processed for in situ hybridization or immunohistochemical evaluation as is well known in the art. This embodiment is designed for detecting mRNA and/or protein markers of apoptosis; i.e., molecules known to be increased or decreased in apoptotic cells. Such markers are well known in the art. For instance, markers known to be increased in apoptotic tissues include, but are not limited to: caspases, annexin, DNAse I, DNAse II, NUC 18/cyclophilin, transglutaminase, Fas, FasL, p53, Diva, Bak, Bcl-$X_9$, Bik, Bim, Bad, Bid, Egl-1, and Bax, to name a few. Markers known to be decreased in apoptotic tissues include, but are not limited to, Bcl2, Bcl-$X_L$, Mcl-1 and CED-9.

As another example, extracts of the tissue segments having various predetermined levels of apoptosis may be prepared for use as controls for Western blots. Method of preparing tissue extracts are well known in the art. Along these same lines, many of the protein markers enumerated above are secreted into the culture medium as the tissue segments undergo apoptosis in a bioreactor or static medium. Accordingly, the culture medium also can be concentrated and used as a control for Western blots in the evaluation of apoptosis in a selected tissue.

The person of skill in the art will be able to appreciate many uses for the apoptosis tissue standards of the present invention. These include uses in basic research, as well as in the clinic.

The apoptosis tissue standards of the invention have clinical utility in diagnosis, prognosis, and evaluation of therapeutic treatments of diseases in which apoptosis, or suppression of apoptosis, is a measurable condition associated with the disease state. One nonlimiting example is the evaluation of mammary tumors, wherein research has already demonstrated that dysregulation of normal programmed cell death mechanisms plays an important role in the pathogenesis and progression of breast cancer (Krajewski et al., Endocrine-Related Cancer 6:29–40, 1999). In accordance with the present invention, a set of apoptosis tissue standards made from normal breast tissue and from breast tumor tissue can be used to comparatively assess a patient's biopsied breast tissue for apoptosis. Further, one or more of those same standards may be used to evaluate regression of the patient's breast tumors as a result of chemotherapy or radiotherapy, by comparison.

As another nonlimiting example, control standards can be utilized to ensure that any assays or tests being utilized in the clinic or research laboratory are performing properly and appropriately on test specimens. Gradations of positive standards can be created and used along with negative controls. The sensitivity and specificity of the test or assay can be evaluated with these standards.

The use of standardized tissue samples for clinical evaluation of diseases in which apoptosis is involved has not been used, nor was it available, prior to the present invention. These standardized controls thus provide the clinician with a level of accuracy and sensitivity (to intermediate gradations of disease) that represent an advance in the art of clinical diagnosis.

The apoptosis tissue standards are also of utility to basic and applied research, wherein the same advances in accuracy and sensitivity are achieved through the use of a standardized set of tissue samples displaying various predetermined levels of apoptosis. For instance, they can be used as positive, negative and intermediate controls in experiments on animals in which a particular therapeutic agent is under evaluation.

As another example, the methodology used to create the apoptosis tissue standards can itself be used as a screening tool for candidate drugs to treat a selected disease state. As an example using the RCCS bioreactor, selected tissue segments are incubated in the bioreactor under conditions known to produce a specific amount of apoptosis. A candidate drug is added to the culture medium, and its effect on the rate of apoptosis is measured.

Also provided in accordance with the present invention are kits to facilitate use of the apoptosis tissue standards of the invention. These may take on many forms, an may include a wide array of different reagents.

A simple kit comprises minimally processed apoptosis tissue standards. For instance, a simple kit may comprise an untreated segment of a selected tissue as a negative control, and a maximally treated tissue segment as a positive control displaying maximum apoptosis. The clinician or investigator utilizes the negative and positive control tissues by processing them along with test tissue samples from the clinic or laboratory, e.g., for histology, immunohistochemistry, TUNEL, or some other evaluative measurement of apoptosis. In a preferred embodiment of this type of kit, tissue samples displaying amounts of apoptosis intermediate between those displayed by the negative and positive controls, respectively, are provided. This graded series of apoptotic tissue samples is used to generate a standard curve for accurately estimating the amount of apoptosis present in the test tissue.

The aforementioned kit may be supplemented with instructions that describe different assays for measuring apoptosis, and additionally with reagents for performing such assays. For example, a set of apoptosis tissue standards may be supplied in a kit that also supplies reagents and instructions for performing TUNEL assays. Alternatively, the kit may comprise antibodies and reagents for performing immunohistochemistry. Other biological molecules and reagents that can be supplied in such kits will be apparent to one skilled in the art, in accordance with customary usage of such kits for the preparation of cells and tissues for these and similar assays.

Another type of kit comprises positive and negative control tissue samples, along with samples of intermediate apoptosis in a preferred embodiment, already processed for a specific type of assay or evaluation. For example, a kit may contain a series of microscope slides containing fixed sections of variously-apoptotic tissues to serve as standards of comparison for histological evaluation of a test tissue. The sections may be further processed by immunohistochemical staining for a selected marker of apoptosis or suppression of apoptosis. These may include any of the markers of apoptosis mentioned previously, or any signal transduction protein involved in the apoptosis pathway. Alternatively, tissue sections already subjected to TUNEL staining can be provided in a kit. A variety of other kits containing the apoptosis tissue standards in a fixed or pre-processed form will be apparent to persons of skill in the art.

The following examples are provided to describe the invention in greater detail. They are intended to illustrate, not to limit, the invention.

EXAMPLE 1

Thymic Apoptosis in Microgravity Culture
Materials and Methods
  The following media and solutions were prepared:

1. Phosphate buffered saline (PBS) for rinsing tissue.
2. Control media, consisting of RPMi 1640 containing 15% heat-inactivated fetal bovine serum, 100 μg/mL penicillin, 100 μg/mL streptomycin, 100 μg/mL L-glutamine, and 2.5 μg/mL amphotericin B.
3. Experimental media, consisting of control media containing 1 μM dexamethasone.

Two microgravity bioreactors (Synthecon, Inc., Houston Tex.) were utilized; one containing control media and one containing experimental media.

The thymus was removed from two Lewis rats, washed in cold PBS to remove blood, and stripped of excess tissue. Thymus tissue was cut into sections of about 3 mm$^3$, while in cold media.

The bioreactors were filled with control (CON) or experimental (DEX) media. Approximately 24 thymus pieces were placed in each bioreactor, for incubation at 37° C. at a rotation speed appropriate for the size of tissue piece and sedimentation rate, in order to provide constant free-fall. Tissue pieces were removed from each bioreactor every half hour for the first 3 hours, then every hour to the sixth hour, then at hour 10 and hour 24.

Tissue was fixed in 10% neutral buffered formalin or Histochoice™ (Amresco, Inc., Solon Ohio), processed to paraffin and sectioned for histochemical analysis. Formalin-fixed sections were stained with hematoxylin and eosin. Immunohistochemical staining for Lewis Y expression was performed with Histochoice TM fixed samples on a DAKO autostainer, using a monoclonal mouse anti-human Lewis Y antibody (DAKO, Carpinteria Calif.). A peroxidase labeled streptavidin-biotin detection system (Zymed, So. San Francisco Calif.) and diaminobenzidine (DAB) chromagen were used.

In situ labeling of apoptosis was measured by terminal deoxynucleotidyl transferase mediated dUTP nick end labeling (TUNEL) method with a cell death detection kit (Boehringer Mannheim Gmbh, Mannheim, Germany). Using digital image analysis, immunostained sections were analyzed for intensity stain index (ISI=[$\Sigma P_0 \times I_0$]/total tissue area in pixels), where P0=number of pixels at each intensity and I0=the intensity units (Doolin et al., J. Surg. Res. 59: 191–197, 1995). TUNEL was quantified as total apoptotic cell number divided by total tissue area.

Results

Results are show in Table 1.

TABLE 1

| Time (Hours) | Percent Area of Stain | | Ratio DEX/CON |
|---|---|---|---|
| | CON | DEX | |
| 0 | 6.04 | 6.04 | 1.00 |
| 3 | 14.86 | 21.68 | 1.46 |
| 6 | 21.08 | 33.29 | 1.58 |
| 10 | 31.92 | 43.82 | 1.37 |
| 24 | 49.83 | 43.30 | 0.87 |

TUNEL assays showed that apoptosis was observable at three hours following initiation of the cultures, and increased in a linear fashion to 10 hours in the dexamethasone culture and to 24 hours in the control culture. Further, at six hours of incubation, apoptosis was demonstrated in free thymocytes infiltrating the media. In the tissue fragments, the inclusion of dexamethasone in the culture media increased the rate of apoptosis up to 10 hours post-initiation, where an apparent maximum was reached. In the control culture (lacking dexamethasone) the rate of apoptosis was comparatively less, but the maximum apoptosis finally reached at 24 hours post-initiation was greater than that observed for the dexamethasone culture. Nonetheless, a time frame was observable for both cultures in which the increase in percentage of apoptotic cells was essentially linear.

EXAMPLE 2

Apoptosis of Several Tissue Types in Microgravity Culture

The experiment described in Example 1 was repeated with each of the following tissue types: heart, kidney, liver, spleen, lymph node and skin. Results paralleled those observed and set forth above for thymic tissue.

EXAMPLE 3

Detection of Apoptosis Markers in Microgravity Cultured Tissues

The experiments described in Examples 1 and 2 were repeated with one or more of the following tissue types: thymus, heart, kidney, liver, spleen, lymph node and skin. Markers of apoptosis were detected immunohistochemically in the treated tissue, and/or by Western blot in culture fluid. Specific apoptosis marker proteins assayed for included annexin, one or more caspases, and Fas/FasL.

Results showed that markers of apoptosis increased in a graded fashion, similar to the results observed from TUNEL assays of the tissues. In addition, the marker proteins accumulated in the culture fluid in a similar graded fashion over time.

This invention is not limited to the embodiments described and exemplified above, but is capable of variation and modification within the scope of the appended claims.

I claim:

1. A composition for use as a standardized measure of apoptosis in a test tissue sample from a subject, the composition comprising:
at least one segment of a naturally occurring tissue that-has been subjected to a treatment that reproducibly results in a predetermined, measurable amount of apoptosis in the segment;
at least a negative control segment of a tissue which has not been subjected to the treatment and at least a positive control segment of the tissue which has been subjected to a level of the treatment that reproducibly results in a maximum amount of apoptosis obtainable in the segment as a result of the treatment; and
one or more intermediate control segments of the tissue which have been subjected to a level of the treatment that reproducibly results in a predetermined amount of apoptosis intermediate between that of the negative control segment and that of the positive control segment.

2. A kit for evaluating apoptosis in a test sample of tissue, the kit comprising:
a container containing at least one segment of a naturally occurring tissue that has been subjected to a treatment that reproducibly results in a predetermined, measurable amount of apoptosis in the segment, and instructions for use of the segment in evaluating the apoptosis in the test sample of tissue;
at least a negative control segment of a tissue which has not been subjected to the treatment and at least a positive control segment of the tissue which has been subjected to a level of the treatment that reproducibly results in a maximum amount of apoptosis obtainable in the segment as a result of the treatment; and one or more intermediate control segments of the tissue which have been subjected to a level of the treatment that reproducibly results in a predetermined amount of apoptosis intermediate between that of the negative control segment and that of the positive control segment.

* * * * *